US012557987B2

(12) United States Patent　　　　(10) Patent No.:　US 12,557,987 B2
　　Sealfon　　　　　　　　　　　　　(45) Date of Patent:　　Feb. 24, 2026

(54) INFRARED IMAGING, MEASUREMENT, AND ANALYSIS OF INFUSION SITES DURING SUBCUTANEOUS AND INTRAVENOUS INFUSIONS

(71) Applicant: INNOVATIVE HEALTH SCIENCES, LLC, Chester, NY (US)

(72) Inventor: Andrew Sealfon, Chester, NY (US)

( * ) Notice: Subject to any disclaimer, the term of this patent is extended or adjusted under 35 U.S.C. 154(b) by 752 days.

(21) Appl. No.: 17/761,418

(22) PCT Filed: Sep. 18, 2020

(86) PCT No.: PCT/US2020/051556
　　§ 371 (c)(1),
　　(2) Date: Mar. 17, 2022

(87) PCT Pub. No.: WO2021/055794
　　PCT Pub. Date: Mar. 25, 2021

(65) Prior Publication Data
　　US 2022/0346648 A1　　Nov. 3, 2022

Related U.S. Application Data

(60) Provisional application No. 62/902,756, filed on Sep. 19, 2019.

(51) Int. Cl.
　　*A61B 5/00*　　　　(2006.01)
　　*A61B 5/01*　　　　(2006.01)
(52) U.S. Cl.
　　CPC ............. *A61B 5/0033* (2013.01); *A61B 5/01* (2013.01); *A61B 2576/00* (2013.01)

(58) Field of Classification Search
　　None
　　See application file for complete search history.

(56) References Cited

U.S. PATENT DOCUMENTS

| 9,843,742 | B2 | 12/2017 | Garrow | |
| 2011/0077527 | A1* | 3/2011 | Yang | ...................... A61B 5/489 |
| | | | | 428/32.6 |
| 2014/0046291 | A1* | 2/2014 | Harris | ............... A61M 5/16836 |
| | | | | 604/503 |
| 2018/0303417 | A1 | 10/2018 | Mensinger | |

* cited by examiner

*Primary Examiner* — Manuel A Mendez
(74) *Attorney, Agent, or Firm* — Carlson, Caspers, Vandenburgh & Lindquist, P.A.

(57)　　　　　　ABSTRACT

A system and method for imaging an anatomical structure corresponding to an infusion therapy anatomical site includes a processor to execute applications stored in a non-transitory computer readable medium, the applications includes a first application to receive imaging information corresponding to radiant energy from the infusion therapy anatomical site, a second application to decompose the received imaging information into discrete image components, a third application to receive at least one of patient biographic profile characteristics and infusion therapy parameters, and a fourth application to receive the discrete image components, the patient biographic profile characteristics and the infusion therapy parameters and to provide a recommended clinical intervention based on at least one of the discrete image components, the patient biographic profile characteristics, and the infusion therapy parameters.

18 Claims, 2 Drawing Sheets

INFRARED IMAGING, MEASUREMENT, AND ANALYSIS OF INFUSION SITES DURING SUBCUTANEOUS AND INTRAVENOUS INFUSIONS

TECHNICAL FIELD

The invention relates generally to infusion pump systems, and more particularly, to infusion pump systems and methods of delivering infusion fluids and measurement of affected infusion sites using infrared imaging.

BACKGROUND

An infusion pump is a medical device that delivers fluids, including nutrients and medications, into a patient in controlled amounts. The nutrients and medications can include insulin, other hormones, antibiotics, chemotherapy drugs, pain relievers, and other fluids. Infusion pumps can be used to deliver fluids intravenously, as well as subcutaneously (beneath the skin), arterially, and epidurally (within the surface of the central nervous system). Infusion pumps can reliably administer fluids in ways that would be impractically expensive, unsafe, or unreliable if performed manually by a nursing staff. Infusion pumps offer advantages over manual administration of fluids, including the ability to deliver fluids in very small volumes and the ability to deliver fluids at precisely programmed rates or automated intervals. For example, infusion pumps can administer 1 ml per hour injections (too small a dose for a drip), injections every minute, injections with repeated boluses requested by the patient, e.g., for patient controlled analgesia (up to a maximum number allowed over a time period), or fluids whose volumes vary by the time of day.

Infusion pump systems often use disposable infusion sets to link the pump system to an infusion site of a patient. These sets usually have tubing between the infusion site and the infusion pump. For constant flow pump systems, the tubing is referred to as an extension set with undefined flow properties. For mechanical pumps, the tubing generally needs to be modified to accommodate flow rate requirements of drugs and fluid viscosity, specifically.

Infusion pumps are frequently used to administer critical fluids, including high-risk medications, so pump failures can have significant consequences for patient safety. Many infusion pumps are fitted with safety features, including alarms and other operator alerts, that activate in the event of a problematic incident. Some pumps alert users when air or another obstruction is detected in the tubing that delivers the infusion fluid to the patient. Smart infusion pumps alert the user when there is a risk of an adverse drug interaction, or when the user programs the operating parameters outside of specified safety limits. An infusion pump system may signal an alarm when an excessive pressure is detected at the pump that is outside a preset safety limit.

Infusion pump systems can cause discomfort or safety concerns for the patient due to excessive pressure in the system that affects the patient's anatomical space, such as when an obstruction in the infusion fluid delivery is encountered or when the infused liquid fills the anatomical space.

One deficiency of current infusion pump systems is their inability to accurately and quickly measure, record, and track affected patient anatomic sites to assess and document adverse treatment reactions and to predict similar reactions.

The above information disclosed in this Background section is only for understanding of the background of the inventive concepts, and, therefore, it may contain information that does not constitute prior art.

SUMMARY

Systems and methods of imaging patient anatomical sites constructed according to the principles and exemplary implementations of the invention, can accurately and quickly measure, record, and/or track affected patient anatomic infusion sites such as subcutaneous and intravenous sites, to assess and/or document adverse treatment reactions and predict similar reactions when delivery of an infusion fluid causes an adverse event. These adverse events can include inflammation, infusion site pain, bruising, edema, erythema, and local swelling. For infusion therapies, forward looking infrared (FLIR) imaging may be useful in assessing peripheral sites for infiltration and extravasation. The systems and methods of imaging and analyzing affected infusion sites constructed according to the principles and exemplary implementations of the invention may use FLIR (forward looking infrared) imaging to collect imaging data, and the transform and analysis of the imaging data using Fast Fourier Transform (FFT) techniques. Some exemplary implementations of the invention also create a database of imaging data, patient data, infusion therapy variables, and patient outcome/treatment data to predict future adverse events based on correlations of the imaging data, patient data, infusion therapy variables, and patient outcome/treatment data.

Thermal imaging captures natural infrared radiation from patient's bodies. One advantage of thermal imaging is that it is completely noncontact, giving no interaction with tissues. It is one of the simplest forms of imaging capable of relaying physiological information. Previously, thermal imaging has been used to diagnose disorders connected with musculoskeletal conditions, peripheral/cerebral vascular conditions, cancer/tumors, deep vein thrombosis, and other conditions. Thermal imaging has also been used for facial vasculature recognition for biometric purposes.

The human body can be viewed as a thermal system that maintains, through thermoregulation, a core body temperature of 36.7° C. Deviations from this core body temperature may cause considerable discomfort. The heat generated by metabolic activities and thermogenesis is conducted through bone, tissue, and skin. The large arteries and veins also play a major role in transferring the temperature to maintain thermal comfort of the human system. Inflammation of blood vessel walls cause variation in blood supply and thereby affects the surface temperature patterns at affected anatomical sites during an infusion. Similarly, bruising, edema, and local swelling also provide different heat signatures when visualized using infrared imaging techniques.

In electric infusion therapy systems, an infusion fluid flow rate is set, for example to 20 ml/hr. As the infusion therapy begins and the infusion fluid is delivered to the patient, and as the infusion progresses, the flow resistance increases. With the increased flow resistance, caused by site saturation or blockages, the infusion pump must increase pressure to continue to deliver the infusion fluid at the set flow rate of 20 ml/hr. As the infusion therapy session progresses, the flow resistance continues to increase, and the infusion pump continues to increase pressure to meet the target 20 ml/hr flow rate. At some point in the infusion therapy session, the pressure becomes so high that an occlusion alarm goes off indicating an unsafe pressure level in the system. These elevated pressures of the infusion fluids delivered to the patient can cause a number of adverse events, including inflammation, infusion site pain, bruising, edema, erythema, and local swelling, as outlined above.

Imaging systems and methods constructed according to the principles and some exemplary implementations of the invention may use an infrared imaging source, such as image capture devices such as thermographic cameras, including a charge-coupled device (CCD), short-mid-long wave infrared cameras, FLIR, Fluke, ICI, Infratec, or other imaging devices than can image or otherwise collect anatomical data of an affected site. For example, an infrared imaging source can identify, measure, and record temperature changes over an affected anatomic area to determine a temperature gradient over the area. The imaging data can be processed using Fast Fourier Transform (FFT) algorithms to extract additional information, using frequency bands that indicate specific pathologies when analyzed. This processed imaging data can be stored as (a) computer file(s) in a computer readable medium in a database of a computer server. The computer file can be appended to associate patient data and infusion therapy parameters with the imaging data. The associated infusion therapy parameters (e.g., drug/fluid data such as drug type, viscosity, volume, adverse effects, and other infusion therapy parameters), infusion fluid flow rate, potential pressure issues of the infusion system used (e.g., constant pressure systems, variable pressure systems, or constant flow systems and the likely operating pressure effects on the outcome), number of needles in the needle set, design of the needle set and tubing (e.g., flow resistance parameters and dimensions), insertion technique (e.g., preparation of patient infusion site, insertion depth, adhesive/bandage used to constrain movement of the needle, insertion errors (e.g., needle inserted wet, fluid leakage during or after infusion, insertion location), needle dimensions/size/depth/material, and other infusion therapy parameters), patient data (e.g., demographic information, patient medical history (e.g., drug-naïve, diagnosis (PIDD, CIDP) etc.), reported pain levels, other treatment site symptoms, and other patient variables) are correlated to identify a variable or variables that can be attributed as causing the adverse event as well as establishing a baseline of achievable data for site assessment and tolerability.

Generally, site reactions caused by the subcutaneous administration of immune globulins will result in some local inflammation, swelling, redness, and other side effects. Inflammation creates an increase in temperature and is detectable by infrared scanning. In some exemplary implementations of the invention, the thermography on the infusion site(s) is performed during the infusion. In many of these cases, FFT and/or differential measurements can actually indicate complications occurring before the patient can detect the discomfort. Interventions and other actions can be taken immediately to address the problems before any harm to the patient occurs. The scans can also be implemented immediately after the infusion is complete. In one exemplary implementation of the invention, the thermography is performed 30 minutes to one hour, or longer, after the completed infusion. The thermography indicates temperature at the infusion site(s) and difference from surrounding tissue(s). Further, comparison of multiple thermographic inputs with respect to rate of change indicates the temperature increase in both direct intensity (in tenths of a degree) as well as areas and temperature gradients. All of this information can be used to determine the intensity of the inflammation and correlate with devices and methods to provide continuous improvement and optimization of the infusion process.

Imaging systems and methods constructed according to the principles and some exemplary implementations of the invention provide infusion patient and system monitoring to ensure accurate and reproducible delivery of an infusion fluid to a patient at a desired anatomical location. By performing infrared imaging and analysis of affected anatomical sites that may result from complications from the infusion therapy treatments, fluid delivery problems, such as occlusions, can be quickly addressed before the patient suffers discomfort or injury. By acquiring, analyzing, and correlating the imaging data, patient data, and treatment data, embodiments of the system and methods of the invention can associate infusion therapy variables and patient variables to outcomes and accurately predict likely causes of treatment events. With this information, future infusion therapy treatments can be modified to avoid variables with likely causation and minimize negative treatment events, such as the amount of pain or discomfort caused by infusion therapies.

Additional features of the inventive concepts will be set forth in the description which follows, and in part will be apparent from the description, or may be learned by practice of the inventive concepts.

According to one aspect of the invention, a system for imaging an anatomical structure corresponding to an infusion therapy anatomical site, the system includes a processor to execute applications stored in a non-transitory computer-readable medium, the applications include: a first application to receive imaging information corresponding to radiant energy from the infusion therapy anatomical site; a second application to decompose the received imaging information into discrete image components; a third application to receive at least one of patient biographic profile characteristics and infusion therapy parameters; and a fourth application to receive the discrete image components, the patient biographic profile characteristics and the infusion therapy parameters and to provide a recommended clinical intervention based on at least one of the discrete image components, the patient biographic profile characteristics, and the infusion therapy parameters.

The imaging information from the anatomical structure corresponding to the infusion therapy anatomical site may include a thermal image.

The thermal image may include measured temperatures and gradients at the infusion therapy anatomical site.

The received imaging information includes a thermal image in a spatial domain and the decomposed imaging information is in a frequency domain.

The second application may include a transforming application to decompose the received imaging information into discrete image components with a basis function and the decomposed imaging information may be generated using a Fast Fourier Transform (FFT) or an inverse Fast Fourier Transform.

The first application may be a receiving application, the second application a transforming application, the third application a profiling application, and the fourth application a recommendation application.

The recommended clinical intervention may include allowing the infusion therapy to continue or stopping the infusion.

The recommended clinical intervention may include one of more of reducing the flow rate of an infused drug; adding an additional infusion site; moving the infusion site to another site on the patient or adjusting one or more of the infusion system parameters.

The infusion system parameters may include the type of needle set, the gauge of the needle, the needle tip design, the type of pump, the location of needle site, and the method of insertion of the needle.

The recommended clinical intervention may include using or removing a dressing or covering for the infusion site, starting or ending administration of pre-medication for the infusion site, and changing the brand of drug being infused, its concentration or volume.

The system may further include: a memory storage device to store (i) the received imaging information corresponding to radiant energy from the infusion therapy anatomical site; (ii) the discrete image components with a basis function; (iii) the received patient biographic profile characteristics and infusion therapy parameters; and (iv) the recommended clinical intervention.

The memory storage device may be configured to store the received imaging information corresponding to radiant energy from the infusion therapy anatomical site and the discrete image components with a basis function and the received patient biographic profile characteristics and infusion therapy parameters and the recommended clinical intervention as at least one of the group of an appended file and linked files.

The recommendation application may be further configured to receive from a multi-patient database at least one of the group of additional discrete image components, additional patient biographic profile characteristics, and additional infusion therapy parameters, and to provide a recommended clinical intervention based on the additional multi-patient database items.

According to another aspect of the invention, a method for imaging anatomical structures corresponding to an infusion therapy patient anatomical site includes the steps of: receiving imaging information at a computer processor, wherein the imaging information corresponds to radiant energy from the infusion therapy patient anatomical site; transforming the received imaging information into discrete image components; receiving patient biographic profile characteristics and infusion therapy parameters; receiving the discrete image components, the patient biographic profile characteristics, and the infusion therapy parameters; and generating a recommended clinical intervention based on at least one of the received discrete image components, patient biographic profile characteristics, and infusion therapy parameters.

The method may further include comprising the step of detecting a radiant energy from the infusion therapy patient anatomical site with a thermal imaging camera; and generating a thermal image with the thermal imaging camera measuring temperatures and gradients of the infusion therapy anatomical site.

The step of receiving the imaging information at the computer processor may be performed during at least one of the group of prior to infusion of the patient, during infusion of the patient, and after infusion of the patient.

The step of transforming the received imaging information may include using a Fast Fourier Transform (FFT) or an inverse Fast Fourier Transform.

The generated recommended clinical intervention may include at least one of allowing the infusion to continue, stopping the infusion, reducing a flow rate of an infused drug, adding an additional infusion site, moving the infusion site to another site on the patient, adjusting one or more of the infusion system parameters, using or removing a dressing or covering for the infusion site, starting or ending administration of pre-medication for the infusion site, and changing the brand of drug being infused, its concentration or volume.

The generated recommended clinical intervention may identify complications with the infusion therapy and be generated prior to the patient identifying the complications or discomfort.

The identified complication with the infusion therapy may be identified based on a rate of change in at least one of the group of temperature, gradient, and size of the anatomical site corresponding to radiant energy from the infusion therapy patient anatomical site.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate exemplary embodiments of the invention, and together with the description serve to explain the inventive concepts.

DETAILED DESCRIPTION

Figure 1:
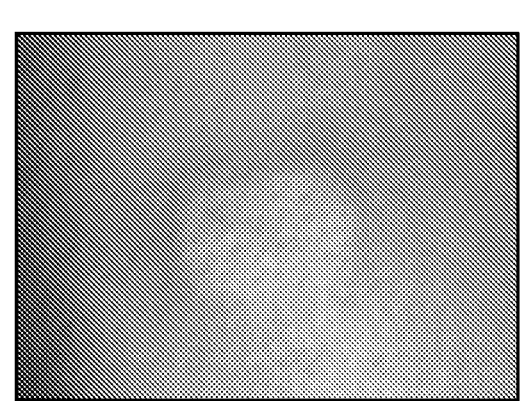
FIG. 1 illustrates an unaided visual view of a typical patient's affected anatomical site post-infusion.

In the following description, for the purposes of explanation, numerous specific details are set forth in order to provide a thorough understanding of various exemplary embodiments or implementations of the invention. As used herein "embodiments" and "implementations" are interchangeable words that are non-limiting examples of devices or methods employing one or more of the inventive concepts disclosed herein. It is apparent, however, that various exemplary embodiments may be practiced without these specific details or with one or more equivalent arrangements. In other instances, well-known structures and devices are shown in block diagram form in order to avoid unnecessarily obscuring various exemplary embodiments. Further, various exemplary embodiments may be different, but do not have to be exclusive. For example, specific shapes, configurations, and characteristics of an exemplary embodiment may be used or implemented in another exemplary embodiment without departing from the inventive concepts.

Unless otherwise specified, the illustrated exemplary embodiments are to be understood as providing exemplary features of varying detail of some ways in which the inventive concepts may be implemented in practice. Therefore, unless otherwise specified, the features, components, modules, layers, films, panels, regions, and/or aspects, etc. (hereinafter individually or collectively referred to as "elements"), of the various embodiments may be otherwise combined, separated, interchanged, and/or rearranged without departing from the inventive concepts.

The use of cross-hatching and/or shading in the accompanying drawings is generally provided to clarify boundaries between adjacent elements. As such, neither the presence nor the absence of cross-hatching or shading conveys or indicates any preference or requirement for particular materials, material properties, dimensions, proportions, commonalities between illustrated elements, and/or any other characteristic, attribute, property, etc., of the elements, unless specified. Further, in the accompanying drawings, the size and relative sizes of elements may be exaggerated for clarity and/or descriptive purposes. When an exemplary embodiment may be implemented differently, a specific process order may be performed differently from the described order. For example, two consecutively described processes may be performed substantially at the same time or performed in an order opposite to the described order. Also, like reference numerals denote like elements.

When an element, such as a layer, is referred to as being "on," "connected to," or "coupled to" another element or layer, it may be directly on, connected to, or coupled to the other element or layer or intervening elements or layers may be present. When, however, an element or layer is referred to as being "directly on," "directly connected to," or "directly coupled to" another element or layer, there are no intervening elements or layers present. To this end, the term "connected" may refer to physical, electrical, and/or fluid connection, with or without intervening elements. Further, the D1-axis, the D2-axis, and the D3-axis are not limited to three axes of a rectangular coordinate system, such as the x, y, and z-axes, and may be interpreted in a broader sense. For example, the D1-axis, the D2-axis, and the D3-axis may be perpendicular to one another, or may represent different directions that are not perpendicular to one another. For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. As used herein, the term "and/or" includes any and all combinations of one or more of the associated listed items.

Although the terms "first," "second," etc. may be used herein to describe various types of elements, these elements should not be limited by these terms. These terms are used to distinguish one element from another element. Thus, a first element discussed below could be termed a second element without departing from the teachings of the disclosure.

Spatially relative terms, such as "beneath," "below," "under," "lower," "above," "upper," "over," "higher," "side" (e.g., as in "sidewall"), and the like, may be used herein for descriptive purposes, and, thereby, to describe one elements relationship to another element(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath" other elements or features would then be oriented "above" the other elements or features. Thus, the exemplary term "below" can encompass both an orientation of above and below. Furthermore, the apparatus may be otherwise oriented (e.g., rotated 90 degrees or at other orientations), and, as such, the spatially relative descriptors used herein interpreted accordingly.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including,"

when used in this specification, specify the presence of stated features, integers, steps, operations, elements, components, and/or groups thereof, but do not preclude the presence or addition of one or more other features, integers, steps, operations, elements, components, and/or groups thereof. It is also noted that, as used herein, the terms "substantially," "about," and other similar terms, are used as terms of approximation and not as terms of degree, and, as such, are utilized to account for inherent deviations in measured, calculated, and/or provided values that would be recognized by one of ordinary skill in the art.

Various exemplary embodiments are described herein with reference to sectional and/or exploded illustrations that are schematic illustrations of idealized exemplary embodiments and/or intermediate structures. As such, variations from the shapes of the illustrations as a result, for example, of manufacturing techniques and/or tolerances, are to be expected. Thus, exemplary embodiments disclosed herein should not necessarily be construed as limited to the particular illustrated shapes of regions but are to include deviations in shapes that result from, for instance, manufacturing. In this manner, regions illustrated in the drawings may be schematic in nature and the shapes of these regions may not reflect actual shapes of regions of a device and, as such, are not necessarily intended to be limiting.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and should not be interpreted in an idealized or overly formal sense, unless expressly so defined herein.

FIG. 1 illustrates an unaided visual view of a typical patient's affected anatomical site post-infusion. Site swelling and inflammation are visibly observable.

Figure 3:
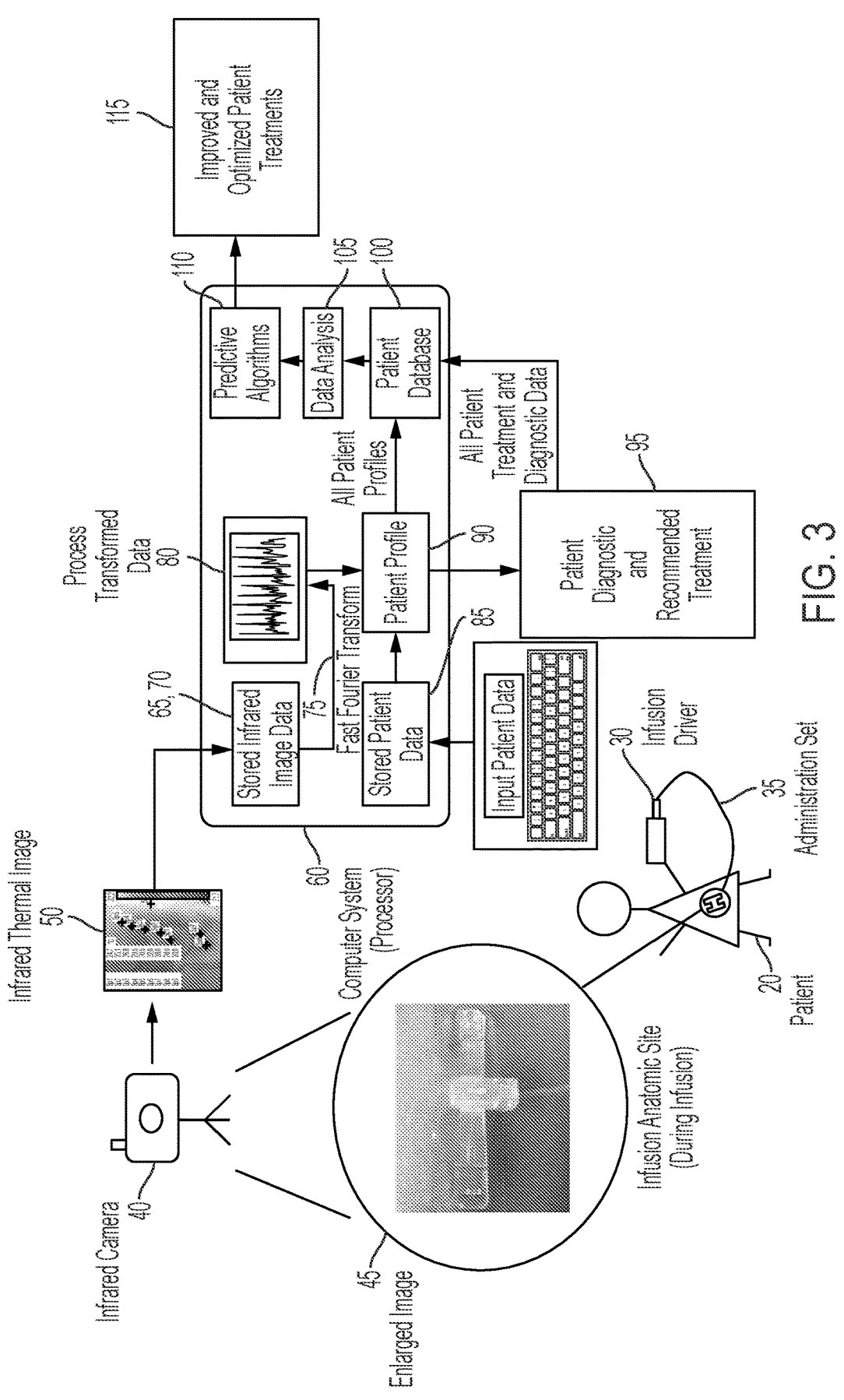
FIG. 3 illustrates an exemplary embodiment of a system constructed according to the principles of the invention using infrared imaging for measurement of subcutaneous and intravenous infusion sites.

FIG. 3 illustrates an exemplary embodiment of a system 10 constructed according to the principles of the invention using infrared imaging for measurement of subcutaneous and intravenous infusion sites. In one example use of the system 10, a patient 20 undergoes an infrared imaging process during a subcutaneous immunoglobulin administration using a portable mechanical infusion system. System 10 is used during infusion therapy of a patient, and an infusion driver 30 is connected to an administration set 35 and delivers an infusion treatment (fluid) to patient 20. The infusion driver 30 can be a mobile(portable) infusion driver, and the administration needle set can deliver medication subcutaneously. Likewise, other types of infusion pumps and infusion fluid reservoirs and delivery devices can be used in exemplary embodiments of the invention depending upon the types of infusion fluids used and the infusion treatment parameters.

Within the clinical or research setting, an infrared imaging device 40 (e.g., a forward-looking infrared (FLIR) thermographic camera) is prepared and calibrated for imaging a patient's infused anatomical site (see FIG. 1). The infrared camera 40 is used to image the anatomical site of the infusion before, during, and/or after the infusion. To reduce error and/or imaging noise, the patient 20 is to be stationary during the imaging process. Infrared camera 40 captures and generates an infrared thermal image 50 of the infusion site (see enlarged image 45 in FIG. 2). By generating real time images of the anatomic site of the infusion, a clinician can immediately identify and address site complications.

Figure 2:
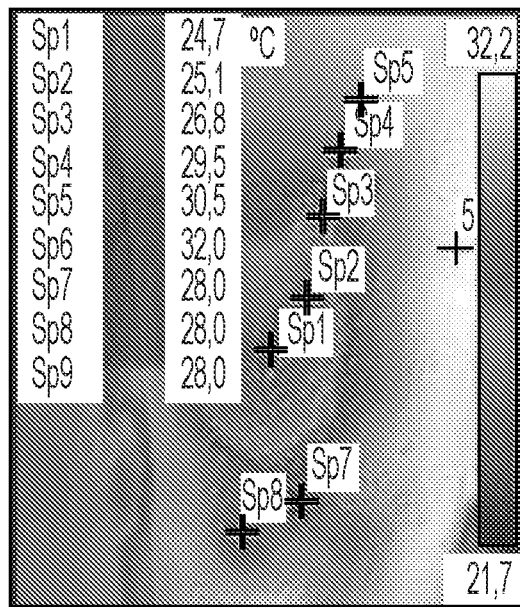
FIG. 2 illustrates a forward-looking infrared (FLIR) image of patient's anatomical site taken post-infusion in accordance with the principles of the invention.

FIG. 2 illustrates a forward-looking infrared (FLIR) image of patient's anatomical site post-infusion. The right-side bar indicates the thermal gradient from 21.7 to 32.2° C. The temperature, in ° C., for 9 spots on and around the patient's anatomic site are indicated by Sp number, in tenths of a degree.

A baseline infrared image 50 of patient's infused anatomic site and nearby tissue is recorded by the camera 40 in which values such as image intensity (temperature) and thermal spread surface area of the site is recorded. The patient 20 then begins the infusion and an infrared image such as shown in at image 45 in FIG. 2 is taken every 5 minutes, in this example. Observing changes in image intensity and thermal spread surface area (among other inputs) with respect to time, a medical professional monitors the rates of change. A rapid increase in temperature and thermal spread surface area can indicate a complication at the infusion site. The medical professional can then appropriately address the complication by stopping the infusion, slowing down the flow rate of the infused drug, adding additional infusion sites, or using another infusion site on the patient's body. In many cases, real time imaging enables a medical professional to prematurely stop the infusion before the patient experiences discomfort and/or adverse site reactions. Based on the thermal gradient rate of change over time at the anatomic site, complications at the infusion site can be predicted, and the infusion therapy can be stopped before the patient even begins to feel discomfort.

Image analysis computer system 60 receives the infrared thermal image 50 and can store the infrared image 50 as an image file 65 in a database 70. The image file 65 can then be processed using Fast Fourier Transform (FFT) 75 techniques to convert the infrared thermal image data from the time and/or space domain into frequency domain. Fast Fourier Transform techniques can include the Cooley-Tukey algorithm, Prime-factor FFT algorithm, Bruun's FFT algorithm, Rader's FFT algorithm, Bluestein's FFT algorithm, Hexagonal FFT algorithm, and other FFT algorithms specialized for real or symmetric data. Once processed, the transformed infrared thermal data (in frequency domain) 80 can now provide more usable and analyzable data of the patient's anatomic site. This transformed data, along with the patient's data 85 including infusion therapy data (described above) can be combined within the patient's profile 90. A medical professional evaluates the patient's infrared image data 80, infusion therapy data (not shown separately), and other patient related data 90 to provide accurate diagnostic and treatment interventions for the patient 95. Such treatment interventions can include optimal drug infusion flow rates, needle penetration depth, and number of needle sites.

The collection of imaging data (65, 80), along with patient data 90, infusion therapy data and treatment data can be stored in a database 70. The different data can be stored in a single file that is appended as it is received by the computer system 60, stored in database 70, and processed using FFT techniques 75. The file can also be linked to stored patient data 85 and patient profile 90. The file(s) can then be stored in patient database 100 and analyzed 105 and used to train predictive models 110 for large data applications (e.g., machine learning, neural networks, etc.) to provide comparison measures related to imaging techniques, infusion techniques, patient biographical information, and likely outcomes over different periods of time. A database of images, FFT transformed imaging data, patient data, and treatment data can be used to generate and train the models using predictive algorithms 110 and pattern recognition to characterize, improve, and optimize patient treatments 115.

The data collected in example above can be pooled and compared with other clinical data previously collected in similar ways—thus providing medical professionals more information so they may provide improved and optimal treatments and intervene sooner.

Also, data patient sensation and discomfort experienced during an infusion can be recorded and correlated to the rate of change in intensity (temperature) and thermal spread surface area data taken from the infrared images. With this information, correlations can be made as to which rates of change and thermal images are indicative of patient pain and discomfort. The imaging process detects and indicates these site complication-related rates of change before the patient experiences pain or discomfort allowing the medical professional to intervene in the infusion process before the patient experiences pain or discomfort.

Pooling together all patient data, infusion therapy data, treatment data, and imaging data provides great clinical predictive insights, which can be used to improve the patient quality of life and satisfaction. Optimal treatment events can be achieved through predictive-related methods using collected patient diagnostic data and infusion therapy parameters (e.g., drug/fluid data such as drug type, viscosity, volume, adverse effects, and other infusion therapy parameters) infusion fluid flow rate, potential pressure issues of the infusion system used (e.g., constant pressure systems, variable pressure systems, or constant flow systems and the likely operating pressure effects on the outcome), number of needles in the needle set, design of the needle set and tubing (e.g., flow resistance parameters and dimensions), insertion technique (e.g., preparation of patient infusion site, insertion depth, adhesive/bandage used to constrain movement of the needle, insertion errors (e.g., needle inserted wet, fluid leakage during or after infusion, insertion location), needle dimensions/size/depth/material, and other infusion therapy parameters), patient data (e.g., demographic information, patient medical history (e.g., drug-naïve, diagnosis (PIDD, CIDP) etc.), reported pain levels, other treatment site symptoms, and other patient variables). Predictive-related methods include the use of computer calculation applications that may analyze collected data and be used to create algorithms that can be used to predict specific variables, diagnostics, and optimal treatment events related to infusions. These predictive algorithms can be made using machine learning, neural networks, pattern recognition and other data analysis techniques.

Examples of specific recommended clinical interventions based upon the imaging data collected by exemplary embodiments of the invention may include, e.g., reducing the flow rate of an infused drug, adding an additional infusion site, moving the infusion site to another site on the patient or adjusting one or more of the infusion system parameters, such as the type of needle set, the gauge of the needle, the needle tip design, the type of pump, the location of needle site (such as hip vs abdomen vs thigh vs back of arm), and the method of insertion of the needle (hand, machine, etc.). Other recommended clinical interventions could include one or more of using or removing a dressing or covering for the infusion site, starting or ending administration of pre-medication for the infusion site, and changing the brand of drug being infused, its concentration, fscig vs scig, volume, etc.

In exemplary embodiments, the computer system 60 and/or one or more components thereof, may be implemented via one or more general purpose and/or special purpose components, such as one or more discrete circuits, digital signal processing chips, integrated circuits, application specific integrated circuits, microprocessors, processors, programmable arrays, field programmable arrays, instruction set processors, and/or the like.

According to one or more exemplary embodiments, the features, functions, processes, etc., described herein may be implemented via software, hardware (e.g., general processor, digital signal processing (DSP) chip, an application specific integrated circuit (ASIC), field programmable gate arrays (FPGAs), etc.), firmware, or a combination thereof. In this manner, infusion system 10 and/or one or more components thereof may include or otherwise be associated with one or more memories (not shown) including code (e.g., instructions) configured to cause the computer system 60, and/or one or more components thereof to perform one or more of the features, functions, processes, etc., described herein.

The memories may be any medium that participates in providing code to the one or more software, hardware, and/or firmware components for execution. Such memories may be implemented in any suitable form, including, but not limited to, non-volatile media, volatile media, and transmission media. Non-volatile media include, for example, optical or magnetic disks. Volatile media include dynamic memory. Transmission media include coaxial cables, copper wire and fiber optics. Transmission media can also take the form of acoustic, optical, or electromagnetic waves. Common forms of computer-readable media include, for example, a floppy disk, a flexible disk, hard disk, magnetic tape, any other magnetic medium, a compact disk-read only memory (CD-ROM), a rewritable compact disk (CD-RW), a digital video disk (DVD), a rewritable DVD (DVD-RW), any other optical medium, punch cards, paper tape, optical mark sheets, any other physical medium with patterns of holes or other optically recognizable indicia, a random-access memory (RAM), a programmable read only memory (PROM), and erasable programmable read only memory (EPROM), a FLASH-EPROM, any other memory chip or cartridge, a carrier wave, or any other medium from which information may be read by, for example, a controller/processor.

Although certain exemplary embodiments and implementations have been described herein, other embodiments and modifications will be apparent from this description. Accordingly, the inventive concepts are not limited to such embodiments, but rather to the broader scope of the appended claims and various obvious modifications and equivalent arrangements as would be apparent to a person of ordinary skill in the art.

What is claimed is:

1. A system for imaging an anatomical structure corresponding to an infusion therapy anatomical site, the system comprising:
   a processor to execute applications stored in a non-transitory computer-readable medium, the applications comprising:
   a first application to receive imaging information corresponding to radiant energy from the infusion therapy anatomical site;
   a second application to decompose the received imaging information into discrete image components and the decomposed imaging information is generated using a Fast Fourier Transform (FFT) or an inverse Fast Fourier Transform;
   a third application to receive at least one of patient biographic profile characteristics and infusion therapy parameters; and a fourth application to receive the discrete image components, the patient biographic profile characteristics and the infusion therapy parameters and to provide a recommended clinical intervention based on at least one of the discrete image components, the patient biographic profile characteristics, and the infusion therapy parameters.

2. The system of claim 1, wherein the imaging information from the anatomical structure corresponding to the infusion therapy anatomical site comprises a thermal image.

3. The system of claim 2, wherein the thermal image comprises measured temperatures and gradients at the infusion therapy anatomical site.

4. The system of claim 1, wherein the first application comprises a receiving application, the second application comprises a transforming application, the third application comprises a profiling application, and the fourth application comprises a recommendation application.

5. The system of claim 1, wherein the recommended clinical intervention comprises allowing the infusion therapy to continue or stopping the infusion.

6. The system of claim 1, wherein the recommended clinical intervention comprises one of more of reducing the flow rate of an infused drug; adding an additional infusion site; moving the infusion site to another site on the patient or adjusting one or more of the infusion system parameters.

7. The system of claim 6, wherein the infusion system parameters comprise the type of needle set, the gauge of the needle, the needle tip design, the type of pump, the location of needle site, and the method of insertion of the needle.

8. The system of claim 1, wherein the recommended clinical intervention comprises using or removing a dressing or covering for the infusion site, starting or ending administration of pre-medication for the infusion site, and changing the brand of drug being infused, its concentration or volume.

9. The system of claim 1 further comprising: a memory storage device to store
   (i) the received imaging information corresponding to radiant energy from the infusion therapy anatomical site;
   (ii) the discrete image components;
   (iii) the received patient biographic profile characteristics and infusion therapy parameters; and
   (iv) the recommended clinical intervention.

10. The system of claim 9, wherein the memory storage device is configured to store the received imaging information corresponding to radiant energy from the infusion therapy anatomical site and the discrete image components and the received patient biographic profile characteristics and infusion therapy parameters and the recommended clinical intervention as at least one of the group of an appended file and linked files.

11. The system of claim 1, wherein the recommendation application is further configured to receives from a multi-patient database at least one of the group of additional discrete image components, additional patient biographic profile characteristics, and additional infusion therapy parameters, and to provide a recommended clinical intervention based on the additional multi-patient database items.

12. The method of claim 1, wherein the step of receiving the imaging information at the computer processor is performed during at least one of the group of prior to infusion of the patient, during infusion of the patient, and after infusion of the patient.

13. The method of claim 1, wherein the generated recommended clinical intervention includes at least one of allowing the infusion to continue, stopping the infusion, reducing a flow rate of an infused drug, adding an additional infusion site, moving the infusion site to another site on the patient, adjusting one or more of the infusion system parameters, using or removing a dressing or covering for the infusion site, starting or ending administration of pre-medication for the infusion site, and changing the brand of drug being infused, its concentration or volume.

14. The method of claim 1, wherein the generated recommended clinical intervention identifies complications with the infusion therapy and is generated prior to the patient identifying the complications or discomfort.

15. The method of claim 14, wherein the identified complication with the infusion therapy is identified based on a rate of change in at least one of the group of temperature, gradient, and size of the anatomical site corresponding to radiant energy from the infusion therapy patient anatomical site.

16. A method for imaging anatomical structures corresponding to an infusion therapy patient anatomical site, the method comprising the steps of:

receiving imaging information at a computer processor, wherein the imaging information corresponds to radiant energy from the infusion therapy patient anatomical site;

transforming the received imaging information into discrete image components using a Fast Fourier Transform (FFT) or an inverse Fast Fourier Transform;

receiving patient biographic profile characteristics and infusion therapy parameters;

receiving the discrete image components, the patient biographic profile characteristics, and the infusion therapy parameters; and generating a recommended clinical intervention based on at least one of the received discrete image components, patient biographic profile characteristics, and infusion therapy parameters.

17. The method of claim 16 further comprising the step of:

detecting a radiant energy from the infusion therapy patient anatomical site with a thermal imaging camera; and generating a thermal image with the thermal imaging camera measuring temperatures and gradients of the infusion therapy anatomical site.

18. A system for imaging an anatomical structure corresponding to an infusion therapy anatomical site, the system comprising:

a processor to execute applications stored in a non-transitory computer-readable medium, the applications comprising:

a first application to receive imaging information corresponding to radiant energy from the infusion therapy anatomical site;

a second application to decompose the received imaging information into discrete image components;

a third application to receive at least one of patient biographic profile characteristics and infusion therapy parameters; and a fourth application to receive the discrete image components, the patient biographic profile characteristics and the infusion therapy parameters and to provide a recommended clinical intervention based on at least one of the discrete image components, the patient biographic profile characteristics, and the infusion therapy parameters;

wherein the received imaging information comprises a thermal image in a spatial domain and the decomposed imaging information is in a frequency domain.

* * * * *